United States Patent [19]

Takasuga et al.

[11] Patent Number: 5,725,634
[45] Date of Patent: Mar. 10, 1998

[54] METHOD FOR COLLECTING IMPURITIES IN THE ATMOSPHERE BY STATE AND APPARATUS FOR ANALYZING THE SAME IN REAL TIME

[75] Inventors: Masami Takasuga, Tenri; Toshio Mukai, Nabari, both of Japan

[73] Assignee: Sharp Kabushiki Kaisha, Osaka, Japan

[21] Appl. No.: 678,695

[22] Filed: Jul. 11, 1996

[30] Foreign Application Priority Data

Aug. 24, 1995 [JP] Japan .................... 7-216231

[51] Int. Cl.$^6$ ............... B01D 53/22; B01D 53/14
[52] U.S. Cl. ............ 95/45; 95/149; 96/4; 96/10; 55/220; 55/270
[58] Field of Search ............... 95/43–45, 47–55, 95/149; 96/4, 5, 10, 14; 55/220, 227, 256, 270

[56] References Cited

U.S. PATENT DOCUMENTS

| | | | |
|---|---|---|---|
| 3,545,931 | 12/1970 | McKinley, Jr. | 95/47 X |
| 3,651,618 | 3/1972 | Klein et al. | 95/44 |
| 3,751,879 | 8/1973 | Allington | 96/5 |
| 3,911,080 | 10/1975 | Mehl et al. | 95/45 X |
| 3,926,561 | 12/1975 | Lucero | 95/45 X |
| 4,201,550 | 5/1980 | Naszticzius et al. | 95/50 X |
| 4,750,918 | 6/1988 | Sirkar | 95/44 |
| 4,772,295 | 9/1988 | Kato et al. | 95/50 |
| 4,915,838 | 4/1990 | Bonne et al. | 95/52 X |
| 4,942,135 | 7/1990 | Zaromb | 95/45 X |
| 5,078,759 | 1/1992 | Kira | 55/256 X |
| 5,143,527 | 9/1992 | Tian-Song | 55/256 X |
| 5,236,474 | 8/1993 | Schofield et al. | 95/47 |
| 5,281,254 | 1/1994 | Birbara et al. | 95/44 |
| 5,395,426 | 3/1995 | Huckins et al. | 95/44 |
| 5,395,589 | 3/1995 | Nacson | 95/47 X |
| 5,490,884 | 2/1996 | Robinson et al. | 95/50 X |
| 5,563,330 | 10/1996 | Kimmig | 55/270 X |

FOREIGN PATENT DOCUMENTS

| | | | |
|---|---|---|---|
| 53-007578 | 1/1978 | Japan | 95/45 |
| 5-302872 | 11/1993 | Japan . | |
| 1380572 | 1/1975 | United Kingdom | 95/43 |
| 2274513 | 7/1994 | United Kingdom . | |

*Primary Examiner*—Robert Spitzer
*Attorney, Agent, or Firm*—Birch, Stewart, Kolasch & Birch, LLP

[57] ABSTRACT

A suction pump draws by suction an atmosphere sample into a gas component collecting section to collect a gas component in the atmosphere into an absorption liquid 48a and thereafter collect a particle component into absorption liquids. A liquid transfer pump transfers the absorption liquids to a measurement standby vessel to make them stand by. When measurement of the absorption liquid is completed, a liquid transfer on-off valve opens to transfer the absorption liquids to an analysis apparatus to make it execute measurement. A liquid transfer pump supplies new absorption liquid when a gas component collecting use absorption liquid vessel and first and second stage impinger sections are emptied. By thus executing collecting, condensation and measurement in parallel by the gas component and the particle component, a state-by-state analysis of the impurities in the atmosphere can be automatically executed in real time.

3 Claims, 8 Drawing Sheets

Fig. 5 tg1, tp1 : Collecting (atmosphere sample suction) time (40 minutes at minimum)
tg2, tp2 : Absorption liquid impurity condensing time (20 minutes at minimum, including cleaning)
tg3, tp3 : Measurement time (20 minutes at minimum)
tp4 : Measurement standby time (20 minutes at minimum)

METHOD FOR COLLECTING IMPURITIES IN THE ATMOSPHERE BY STATE AND APPARATUS FOR ANALYZING THE SAME IN REAL TIME

BACKGROUND OF THE INVENTION

1. Field of the Invention

The present invention relates to a method for collecting impurities in an atmosphere inside a clean room and an apparatus for analyzing the impurities in the atmosphere.

2. Description of the Prior Art

In a clean room of a semiconductor manufacturing plant, a variety of chemicals such as HF, $H_2SO_4$ and $NH_4OH$ are used, and it is known that the gases generated from the chemicals exert various bad influences. For example, HF resolves a glass fiber filter material of an HEPA (High-Efficiency Particulate Air) filter and generates B (Boron) contamination to affect the characteristics of semiconductors. Besides, $NH_3$ affects a chemically amplified resist for executing fine processing. Furthermore, when a plurality of these several kinds of gas components exist, the gas components grow into particles through chemical reactions to cause dust.

As a countermeasure against the atmospheric contamination, filters are generally used. It is to be noted that different filters are used for the removal of gas and particle. In the case of gas, a chemical filter employing an activated carbon or an ion exchange resin is used, while the HEPA filter or the like is used in the case of particle.

Furthermore, in order to correctly ascertain the contaminant, it is important to correctly evaluate the impurities in the atmosphere. For the above purpose, it is required to evaluate the impurities in the atmosphere in real time by state (gas, particle and so forth) and speedily feed the evaluation result back to an atmosphere control of the plant.

Figure 7:
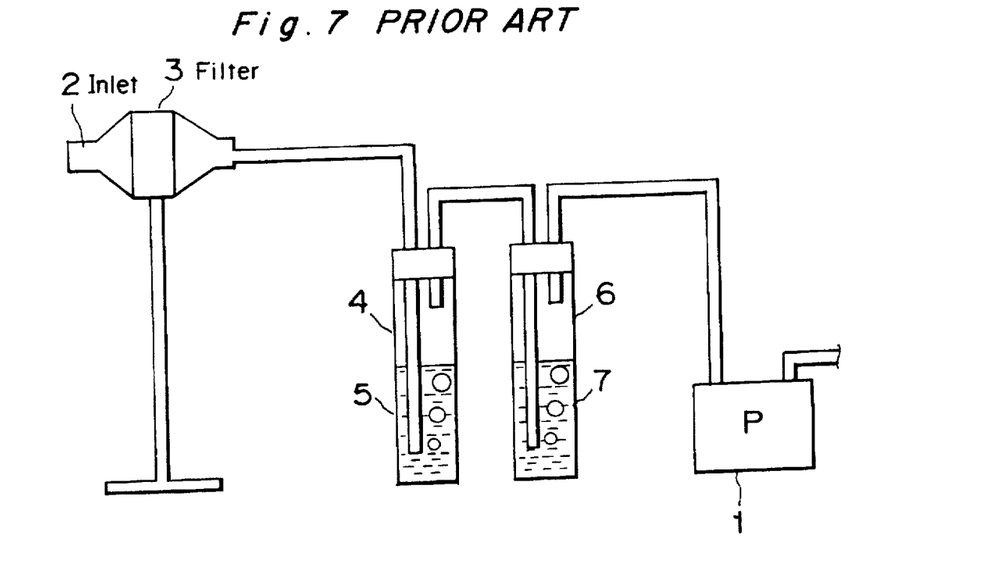
FIG. 7 is an explanatory view of a prior art gas component collecting method.

Conventionally, when collecting a gas component, the gas component has been collected by a method as shown in FIG. 7. According to this method, particles in the atmosphere which are taken in from an atmosphere sample intake 2 by the operation of an atmosphere sample suction pump 1 are removed by a particle component collecting filter paper 3. Subsequently, the atmosphere is put through gas component collecting use absorption liquids 5 and 7 to be subjected to bubbling in a first stage impinger section 4 and a second stage impinger section 6, so that the gas component is collected.

Figure 8:
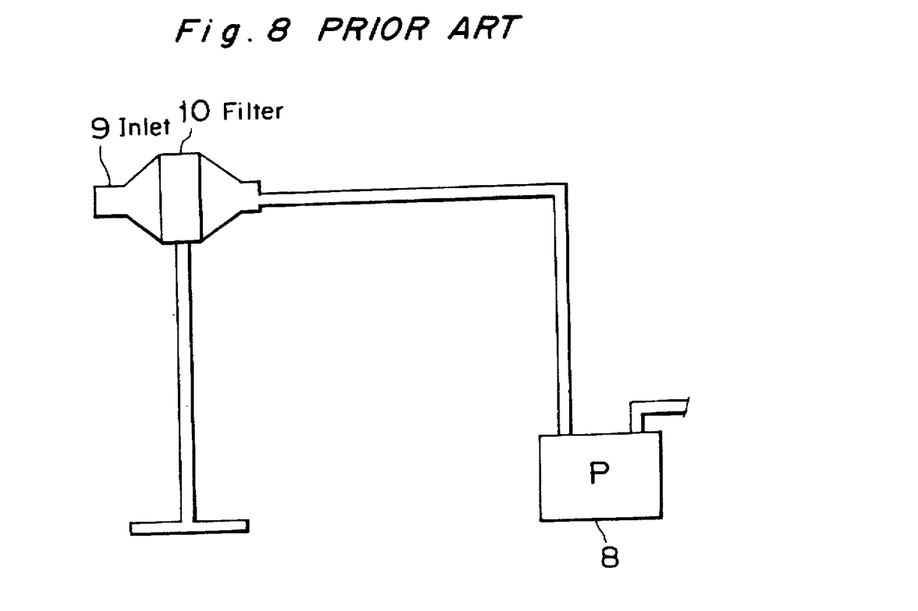
FIG. 8 is an explanatory view of a prior art particle component collecting method.

On the other hand, when collecting a particle component, as shown in FIG. 8, it is general to collect particles by putting an atmosphere which is taken in from an atmosphere sample intake 9 through a particle component collecting filter paper 10 by the operation of an atmosphere sample suction pump 8.

Figure 9:
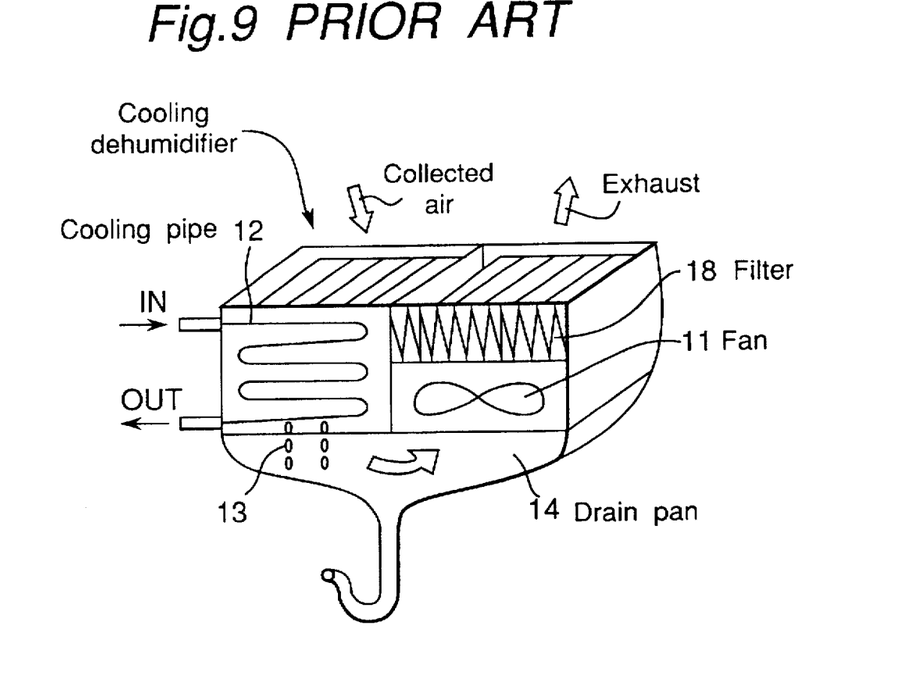
FIG. 9 is an external view of a cooling dehumidifier in a prior art atmosphere analysis apparatus.
Figure 10:
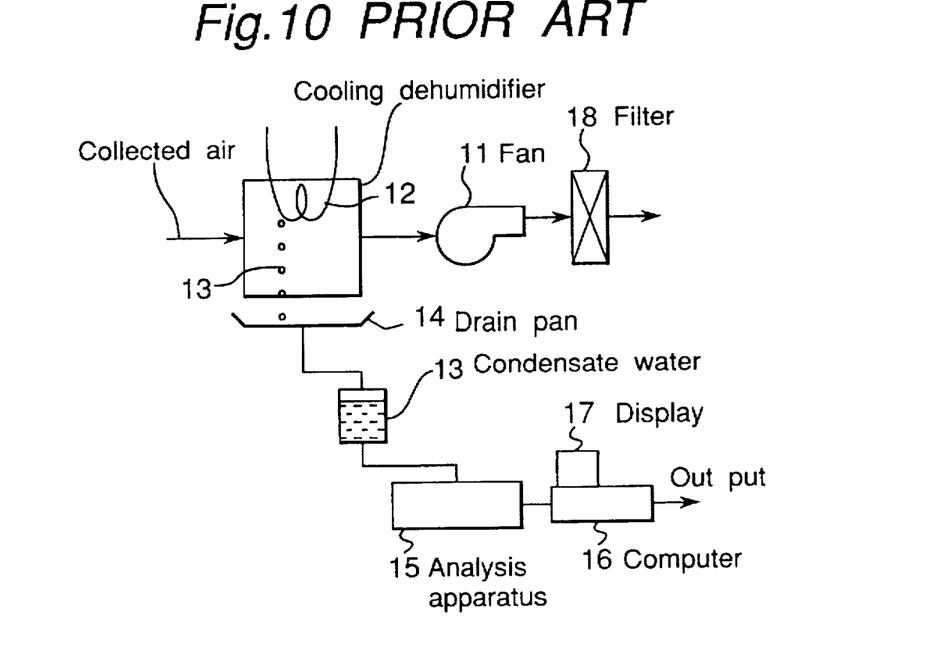
FIG. 10 is a general view of the atmosphere analysis apparatus including the cooling dehumidifier shown in FIG. 9.

There is another atmosphere analysis apparatus as shown in FIGS. 9 and 10 (Japanese Patent Laid-Open Publication No. HEI 5-302872). This analysis apparatus operates as follows to analyze the impurities in the atmosphere inside a clean room.

That is, a fan 11 is operated to guide the clean room atmosphere into a cooling dehumidifier having a cooling pipe 12 so as to condense its moisture into water 13. The condensate water 13 is received by a drain pan 14 and transferred to an analysis apparatus 15. Then, the impurities contained in the condensate water 13 are analyzed by the analysis apparatus 15 under the control of a computer 16, and the analysis result is displayed on a display 17. It is to be noted that the air from which the moisture has been removed is put through a filter 18 to be discharged.

However, the gas component collecting method as shown in FIG. 7 has the following problem.

That is, when analyzing the collected gas component, the gas component collecting use absorption liquids 5 and 7 in both the impinger sections 4 and 6 are introduced into the analysis apparatus. However, since the filter paper 3 is used for the removal of the particles, when the atmosphere contains particle components having a very high volatility (e.g., $NH_4NO_3$), the particle components are possibly gasified by the influence of the moisture of the atmosphere, so that the gasified particle components will pass through the filter paper 3 to be mixed in the gas component. Therefore, an error may take place in the analysis result, causing an accuracy problem.

On the other hand, the particle component collecting method as shown in FIG. 8 has the following problems.

That is, when analyzing the collected particle component, it is required to extract the particle component collected on the filter paper 10 by an acid solution and then introduce the solution into the analysis apparatus. Therefore, when a particle component having a high volatility is contained, the particles will be gasified to possibly cause an error in the analysis result. Furthermore, there is such a problem that the analysis can be hardly automated due to the increase of blank values accompanied by an extraction preprocessing by means of the filter paper and the inefficiency of the extracting work.

Accordingly, in order to monitor the impurities in the atmosphere inside the clean room only by the impingers without using filter paper, it is required to collect the impurities in the atmosphere inside the clean room for a specified time by an apparatus obtained by removing the filter paper 3 from the structure shown in FIG. 7 and execute analysis by collecting the collecting use absorption liquids 5 and 7. However, as of today, the analysis of the collecting use absorption liquids 5 and 7 are required to be executed manually. Therefore, a degraded efficiency results, and there is the problem of an error due to the possible occurrence of contamination accompanied by the manual work. Therefore, it is hard to achieve a high-sensitivity measurement and short-time measurement, and it is impossible to perform monitoring of the impurities in the atmosphere inside the clean room in real time. Also, there is such a problem that the impurities in the atmosphere cannot be analyzed by state.

Furthermore, the atmosphere analysis apparatuses as shown in FIGS. 9 and 10 have such a problem that the impurities cannot be analyzed through discrimination between the states thereof (gas, particle and so forth). Furthermore, an impurity collecting section comprised of the cooling dehumidifier having the fan 11, cooling pipe 12, drain pan 14 and filter 18 has no cleaning function. Therefore, the contamination generated in each time of analysis will accumulate to possibly cause a great measurement error, reducing the reliability of the analysis result and creating a problem.

SUMMARY OF THE INVENTION

The object of the present invention is therefore to provide an in-atmosphere impurity collecting method capable of collecting the impurities in an atmosphere by state, an in-atmosphere impurity automatic analysis apparatus capable of automatically analyzing the impurities in the atmosphere in real time and an in-atmosphere impurity state-by-state analysis apparatus capable of analyzing the impurities in the atmosphere by state in real time.

In order to achieve the aforementioned object, there is provided an in-atmosphere impurity collecting method comprising the steps of:

introducing an atmosphere into a gas component permeable membrane tube so as to collect a gas component in the atmosphere into a first absorption liquid which is put in contact with an outer peripheral surface of the gas component permeable membrane tube; and introducing into an impinger the atmosphere which has been put inwardly through the gas component permeable membrane tube and from which the gas component has been collected and subjecting the atmosphere to bubbling in a second absorption liquid so as to collect a particle component in the atmosphere;

thereby collecting impurities in the atmosphere as the gas component and the particle component separately from each other.

According to the collecting method of the embodiment of the present invention, the gas component and the particle component are separately collected in the different absorption liquids through the one operation of introducing the atmosphere into the impingers after putting the atmosphere through the gas component permeable membrane tube.

Also, there is provided an in-atmosphere impurity automatic analysis apparatus comprising:

an impinger which receives therein an absorption liquid for impurities in an atmosphere;

a suction pump which sucks a gas inside the impinger to take the atmosphere into the impinger and subjects the atmosphere to bubbling in the absorption liquid so that it collects the impurities in the atmosphere;

a first liquid transfer pump which transfers the absorption liquid containing the impurities in the atmosphere to an analysis apparatus;

a second liquid transfer pump which supplies the absorption liquid in an absorption liquid supply tank to the impinger from which the absorption liquid has been transferred; and a control means for controlling operations of the suction pump, the first liquid transfer pump and the second liquid transfer pump to make them execute continuously repetitively the collecting of the impurities in the atmosphere, the transfer of the absorption liquid to the analysis apparatus and the supply of the absorption liquid.

In the automatic analysis apparatus of the embodiment of the present invention, when the suction pump is driven to, suck the gas in the impinger under the control of the control means, the atmosphere is taken into the impinger to be subjected to bubbling in the absorption liquid, so that the impurities in the atmosphere are collected into the absorption liquid. Then, the first liquid transfer pump is driven to transfer the absorption liquid containing the impurities to the analysis apparatus. Then, the second liquid transfer pump is driven to supply new absorption liquid to the emptied impinger.

Thus, the following processes are repetitively executed; collecting the impurities in the atmosphere transferring the absorption liquid to the analysis apparatus→supplying new absorption liquid→collecting the impurities in the atmosphere→. . . , so that the impurities in the atmosphere are automatically analyzed in real time.

Also, there is provided an in-atmosphere impurity state-by-state analysis apparatus comprising:

a gas component collecting section which comprises a cylindrical gas component absorption liquid vessel whose both ends are closed, a gas component permeable membrane tube which is inserted in the gas component absorption liquid vessel with its both ends fitted close to both end surfaces of the gas component absorption liquid vessel, and a gas component absorption liquid which is filled inside the gas component absorption liquid vessel while being put in contact with an outer peripheral surface of the gas component permeable membrane tube, wherein the gas component absorption liquid vessel has at its one and the other end surfaces an atmosphere -inlet and -outlet respectively which communicate with the inside of the gas component permeable membrane tube;

an impinger which receives therein a particle component absorption liquid and of which the atmosphere intake communicates with the atmosphere-outlet of the gas component collecting section;

a suction pump which sucks the gas inside the impinger to take the atmosphere into the gas component permeable membrane tube, make the gas component absorption liquid collect the gas component in the atmosphere, and thereafter take the atmosphere being rid of the gas component into the impinger to subject the atmosphere to bubbling in the particle component absorption liquid so that it collects a particle component in the atmosphere;

a first liquid transfer means for transferring the particle component absorption liquid containing the particle component to a measurement standby vessel so as to make the liquid stand by;

a second liquid transfer means for transferring the gas component absorption liquid containing the gas component to the analysis apparatus while the particle component absorption liquid is made to stand by;

a third liquid transfer means for supplying the absorption liquid in an absorption liquid supply tank to the gas component absorption liquid vessel and to the impinger when the absorption liquid inside the gas component absorption liquid vessel and the adsorption liquid inside the impinger are transferred;

a fourth liquid transfer means for transferring the particle component absorption liquid that is standing by in the measurement standby vessel to the analysis apparatus when the analysis of the gas component absorption liquid by the analysis apparatus is completed; and a control means for controlling operations of the suction pump and the first through fourth liquid transfer means to make them execute continuously repetitively the collecting of the impurities in the atmosphere by the gas component and the particle component, the standing-by of the particle component absorption liquid, the transfer of each absorption liquid to the analysis apparatus and the supply of the absorption liquid to the gas component absorption liquid vessel and the impinger.

In the state-by-state analysis apparatus of the embodiment of the present invention, when the suction pump is driven to suck the gas in the impinger under the control of the control means, the atmosphere is taken into the gas component permeable membrane tube forming a part of the gas component collecting section and communicating with the impinger, so that the gas component in the atmosphere is collected in the gas component absorption liquid. Further, the atmosphere being rid of the gas component is taken into the impinger to be subjected to bubbling in the particle component absorption liquid, so that the liquid collects the particle component in the atmosphere. Then, the first liquid transfer means is operated to transfer the particle component absorption liquid containing the particle component to the measurement standby vessel to be made to stand by, while the second liquid transfer means is operated to transfer the gas component absorption liquid containing the gas component to the analysis apparatus.

Then, the third liquid transfer means is operated to supply new absorption liquid to the emptied gas component absorption liquid vessel and the impinger. When the analysis of the gas component absorption liquid by the analysis apparatus is completed, the fourth liquid transfer means is operated to transfer the particle component absorption liquid that is standing by in the measurement standby vessel to the analysis apparatus.

Thus, the following processes are repetitively executed; collecting of the impurities state-by-state in the atmosphere→standing-by of the particle component absorption liquid→transferring the gas component absorption liquid to the analysis apparatus so that the impurities in the atmosphere are analyzed by state in real time.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

The present invention will be described below based on the embodiments thereof with reference to the accompanying drawings.

Figure 1:
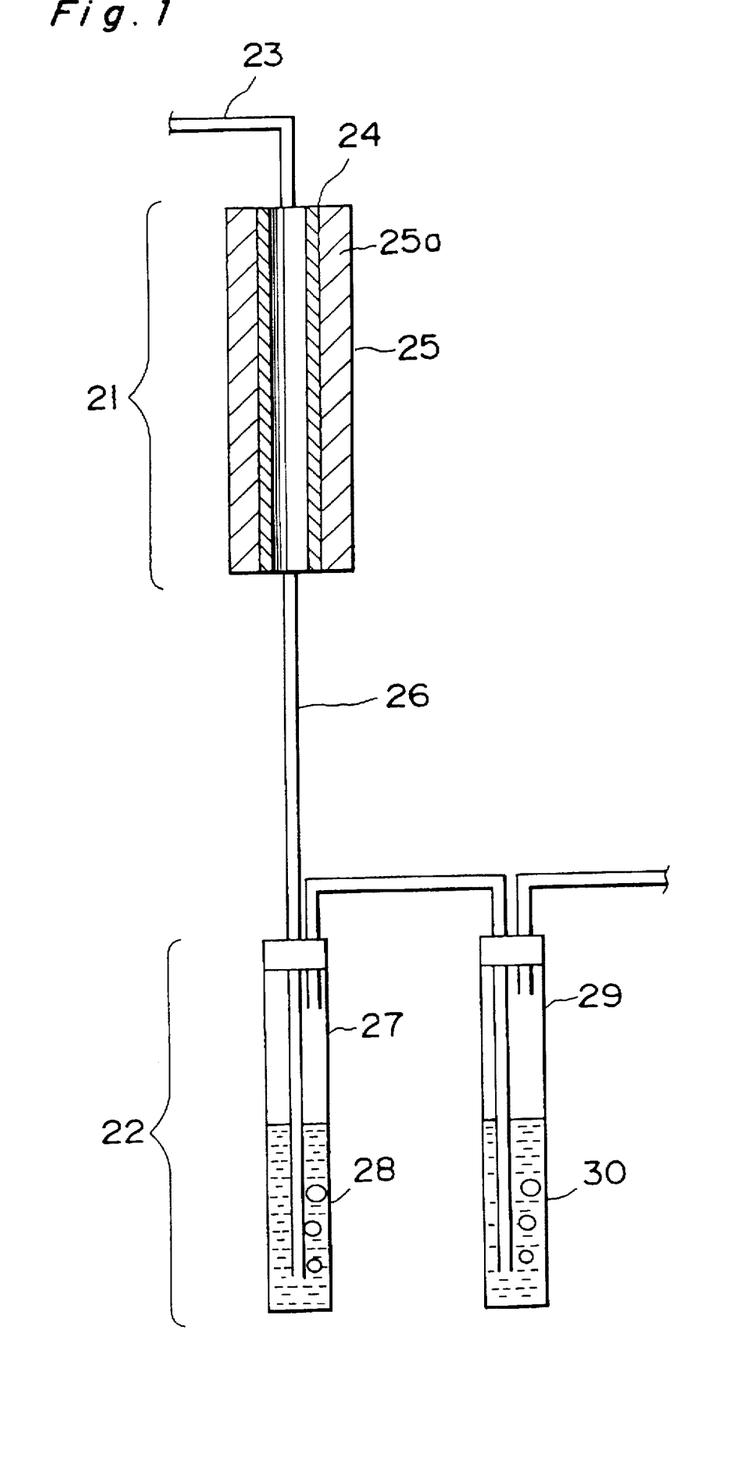
FIG. 1 is a schematic view of an in-atmosphere impurity collecting apparatus for implementing an in-atmosphere impurity collecting method of the present invention.

FIG. 1 is a schematic view of an in-atmosphere impurity collecting apparatus according to the present embodiment.

An in-atmosphere impurity collecting method will be described below with reference to FIG. 1.

The in-atmosphere impurity collecting apparatus of the present embodiment is constituted broadly by a gas component collecting section 21 and a particle component collecting section 22.

The gas component collecting section 21 comprises: a cylindrical gas component collecting use absorption liquid vessel 25 whose both ends are closed; a cylindrical gas component permeable membrane tube 24 which is formed of porous polytetrafluoroethylene or the like and is inserted in the gas component collecting use absorption liquid vessel 25 with its both ends fitted close to both the end surfaces of the gas component collecting use absorption liquid vessel 25; and a gas component collecting use absorption liquid 25a which is filled inside the gas component collecting use absorption liquid vessel 25 while being put in contact with an outer peripheral surface of the gas component permeable membrane tube 24. Then, both the end surfaces of the gas component collecting use absorption liquid vessel 25 are connected to an atmosphere sample intake pipe 23 and a joint tube 26 which are communicated with the inside of the gas component permeable membrane tube 24.

On the other hand, the particle component collecting section 22 comprises: a first stage impinger section 27 which receives therein a first stage particle component collecting use absorption liquid 28; and a second stage impinger section 29 which receives therein a second stage particle component collecting use absorption liquid 30.

The in-atmosphere impurity collecting apparatus operates as follows.

First, an atmosphere sample taken in from the atmosphere sample intake pipe 23 passes through the inside of the gas component permeable membrane tube 24 of the gas component collecting section 21. At this moment, a gas component in the atmosphere sample is collected in the gas component collecting use absorption liquid 25a after permeating through the gas component permeable membrane tube 24 by its own diffusion in the radial direction in the atmosphere sample. It is to be noted that pure water is used as the gas component collecting use absorption liquid 25a.

The atmosphere sample from which the gas component has been thus removed is guided through the joint tube 26 to the particle component collecting section 22. Then, after being subjected to bubbling in the first stage particle component collecting use absorption liquid 28 inside the first stage impinger section 27, the atmosphere sample is subjected to bubbling again in the second stage particle component collecting use absorption liquid 30 inside the second stage impinger section 29. Thus, the particle component in the atmosphere is collected in the first stage particle component collecting use absorption liquid 28 and the second stage particle component collecting use absorption liquid 30.

It is to be noted that the first stage particle component collecting use absorption liquid 28 and the second stage particle component collecting use absorption liquid 30 are implemented by pure water in the case where an acid component and an ammonium component are analyzed, or by a diluted acid solution in the case where a metal component is analyzed.

Furthermore, the two impinger sections of the first stage impinger section 27 and the second stage impinger section 29 are used for the purpose of collecting in the second stage impinger section 29 each particle component which has not been able to be collected in the first stage impinger section 27.

As described above, according to the in-atmosphere impurity collecting method by means of the above in-atmosphere impurity collecting apparatus, by firstly collecting the gas component into the gas component collecting use absorption liquid 25a and thereafter collecting the particle component into the first and second stage particle component collecting use absorption liquids 28 and 30, the impurities in the atmosphere can be simultaneously collected while being separated into the gas component and the particle component.

Furthermore, since the impurities in the atmosphere are separated into the gas component and the particle component with no filter paper being used, the impurities in the atmosphere can be surely separated into the gas component and the particle component even when a highly volatile particle component is included in the atmosphere.

Table 1 shows results of ICA (Ion Chromato-Analyzer)-evaluation of the impurities in the atmosphere inside the clean room collected by the above in-atmosphere impurity collecting apparatus.

can be evaluated by state (gas and particle). Therefore, an appropriate countermeasure against the impurities in the atmosphere can be taken, and this means that the method is very effective.

An in-atmosphere impurity automatic analysis apparatus capable of automatically analyzing impurities in the atmosphere by means of an impinger will be described next with reference to FIG. 2.

In this in-atmosphere impurity automatic analysis apparatus, an atmosphere sample suction pump 40 sucks the gas inside a first and a second stage impinger sections 32, 34 of an impinger section 31 having the same construction as that of the particle component collecting section 22 shown in FIG. 1, a collecting use absorption liquid transfer pump 41 introduces collecting use absorption liquids 33 and 35 for both the impinger sections 32 and 34 into a measurement standby vessel 42 and an absorption liquid supply use liquid transfer pump 38 supplies a collecting use absorption liquid in an absorption liquid supply tank 37 to both the impinger sections 32 and 34.

| Collection | Clean room atmosphere analysis results (relative values) | | | | | | | | | | | |
|---|---|---|---|---|---|---|---|---|---|---|---|---|
| | F$^-$ | | Cl$^-$ | | NO$_2^-$ | | NO$_3^-$ | | SO$_4^{2-}$ | | NH$_4^+$ | |
| place | gas | particle | gas | particle | gas | particle | gas | particle | gas | particle | gas | particle |
| A | N.D | N.D | N.D | 1.00 | 7.30 | 1.00 | 0.06 | 1.36 | N.D | 0.52 | 12.1 | 2.88 |
| B | 0.30 | 0.46 | 0.04 | 0.12 | 9.26 | 4.48 | 0.02 | 0.46 | 0.06 | 0.32 | 8.32 | 0.46 |
| C | 0.32 | 6.46 | N.D | 0.74 | 6.62 | 2.38 | 0.02 | 0.98 | 0.06 | 1.94 | 9.02 | 7.00 |
| D | 0.56 | 5.72 | 0.04 | 0.64 | 9.90 | 1.34 | 0.04 | 1.18 | 0.28 | 1.50 | 3.90 | 2.40 |
| E | 0.58 | 1.04 | 0.04 | 0.40 | 11.0 | 4.58 | 0.04 | 0.98 | 0.20 | 1.34 | 2.54 | 4.28 |

Note: N.D means no detection.

According to Table 1, it can be found that a greater amount of NH$_4^+$ gas component is detected in the collection place A, and it is required to mount a chemical filter for removing the gas component and specify the contamination source of the NH$_4^+$ gas component.

Furthermore, the collection places B and C are in the vicinity of the same processing apparatus in the clean room, and it can be found that particle components of most impurities are detected greatly in amount at the rear side, or utility area of the apparatus (collection place C) than at the front side, or the processing area of the apparatus (collection place B). These analysis results conform to the difference in cleanliness between the processing area and the utility area inside the clean room, and prove that the collecting method by the above in-atmosphere impurity collecting apparatus is excellent. It is to be noted that F$^-$ gas component is detected in the collection place B, and this fact indicates that much care is required to be taken for the B (Boron) contamination from the glass fiber filter material of the HEPA filter.

Furthermore, the collection places D and E are the places where the collecting is executed for the purpose of evaluating a chemical filter, consequently comparing IN side (collection place D) with OUT side (collection place E) of an ammonium removing chemical filter. According to this comparison, the NH$_4^+$ gas component on the OUT side is reduced only by about 30 percent compared with that on the IN side of the chemical filter. Judging from the fact that this chemical filter has a capacity of removing not less than 90 percent of the NH$_4^+$ gas component, it can be decided that the chemical filter has come into a stage when it is to be replaced.

By thus using the above in-atmosphere impurity collecting method, the amount of the impurities in the atmosphere The in-atmosphere impurity automatic analysis apparatus constructed as above operates as follows to automatically monitor the impurities in the atmosphere in real time.

That is, when the gases inside the first and the second stage impinger sections 32, 34 are sucked via a flow meter 39 by the atmosphere sample suction pump 40, an atmosphere sample is taken into the impinger section 31 at a constant flow rate. The atmosphere sample thus taken in is subjected to bubbling in the first stage impinger section 32, so that the impurities are collected into the first stage collecting use absorption liquid 33. Then, each impurity which has not been collected in the first stage impinger section 32 is subsequently subjected to bubbling again in the second stage impinger section 34, so that each impurity is collected into the second stage collecting use absorption liquid 35.

It is to be noted that the first and the second stage collecting use absorption liquids 33, 35 are supplied from the absorption liquid supply tank 37 via a liquid transfer on-off valve 43a by the absorption liquid supply use liquid transfer pump 38, while the liquid supply amount is adjusted to a specified amount by a liquid surface sensor 36.

When the atmosphere sample is sucked in by suction for a specified time to complete the collecting operation, the liquid amounts of the collecting use absorption liquids 33 and 35 in the impinger sections 32 and 34 are reduced. Therefore, by the operations of the absorption liquid supply use transfer pump 38 and the liquid surface sensor 36, the collecting use absorption liquids 33 and 35 are supplied to a specified amount (i.e., to the liquid amount prior to the start of the collecting operation). Thereafter, the collecting use absorption liquids 33 and 35 are introduced into the measurement standby vessel 42 by the collecting use absorption liquid transfer pump 41, so that the collecting use absorption liquids 33 and 35 are mixed with each other. Then, a liquid transfer on-off valve 43d is opened to transfer the collecting use absorption liquid in the measurement standby vessel 42 to an analysis apparatus (not shown) such as a two-way simultaneous measurement ion chromato-analyzer based on, for example, a condensed column method to execute an analysis.

By thus providing the measurement standby vessel 42, the collecting use absorption liquids 33 and 35 in the respective two impinger sections 32 and 34 can be measured at a time.

Further, by using the analysis apparatus based on the condensed column method as the analysis apparatus, a correct analysis can be achieved even when the amount of the collected impurities is small due to a short collecting time.

By repeating the above operations, real time monitoring of the impurities in the atmosphere is performed automatically.

In the above case, the liquid transfer on-off valves 43b and 43c are opened to transfer both the collecting use absorption liquids 33 and 35 to the measurement standby vessel 42, and then the liquid transfer on-off valve 43a is opened to supply new collecting use absorption liquid to both the impinger sections 32 and 34. Therefore, the collecting use absorption liquids 33 and 35 inside the respective first and second stage impinger sections 32, 34 are replaced for every analysis of impurities, so that the first stage impinger section 32 and the second stage impinger section 34 are internally cleaned. That is, the present in-atmosphere impurity automatic analysis apparatus has a cleaning function, and the cleaning function can be obtained in accordance with the timing of opening and closing the liquid transfer on-off valves 43a through 43c in each time of collecting.

As described above, the in-atmosphere impurity automatic analysis apparatus of the present embodiment is provided with the impingers, and the atmosphere sample suction pump 40 is driven to draw the atmosphere sample by suction into the first and second stage impinger sections 32 and 34 so as to collect the impurities into both the collecting use absorption liquids 33 and 35. Then, by driving the collecting use absorption liquid transfer pump 41, both the collecting use absorption liquids 33 and 35 are introduced into the measurement standby vessel 42 to be mixed with each other, and then transferred to the analysis apparatus to be condensed and measured.

Therefore, according to the present in-atmosphere impurity automatic analysis apparatus, the collecting and measurement of the impurities can be automatically executed to allow automatic monitoring of the impurities in the atmosphere to be achieved.

Furthermore, the collecting use absorption liquids 33 and 35 inside the respective first and the second stage impinger sections 32, 34 are replaced in accordance with the timing of opening and closing the liquid transfer on-off valves 43a through 43c in each time of collecting, so that both the impinger sections 32 and 34 are cleaned. That is, the present in-atmosphere impurity automatic analysis apparatus has a cleaning function.

It is to be noted that each of the first and second stage impinger sections 32 and 34 of the present embodiment has a shape elongated more than that of the prior art impinger for the purpose of reducing the amount of the collecting use absorption liquids 33 and 35 and assuring an increased time of contact between the bubbles generated by the bubbling and the collecting use absorption liquids 33 and 35.

An in-atmosphere impurity state-by-state analysis apparatus which is provided with the in-atmosphere impurity collecting apparatus shown in FIG. 1 and is capable of automatically analyzing the impurities in the atmosphere by state will be described next with reference to FIG. 3.

Figure 2:
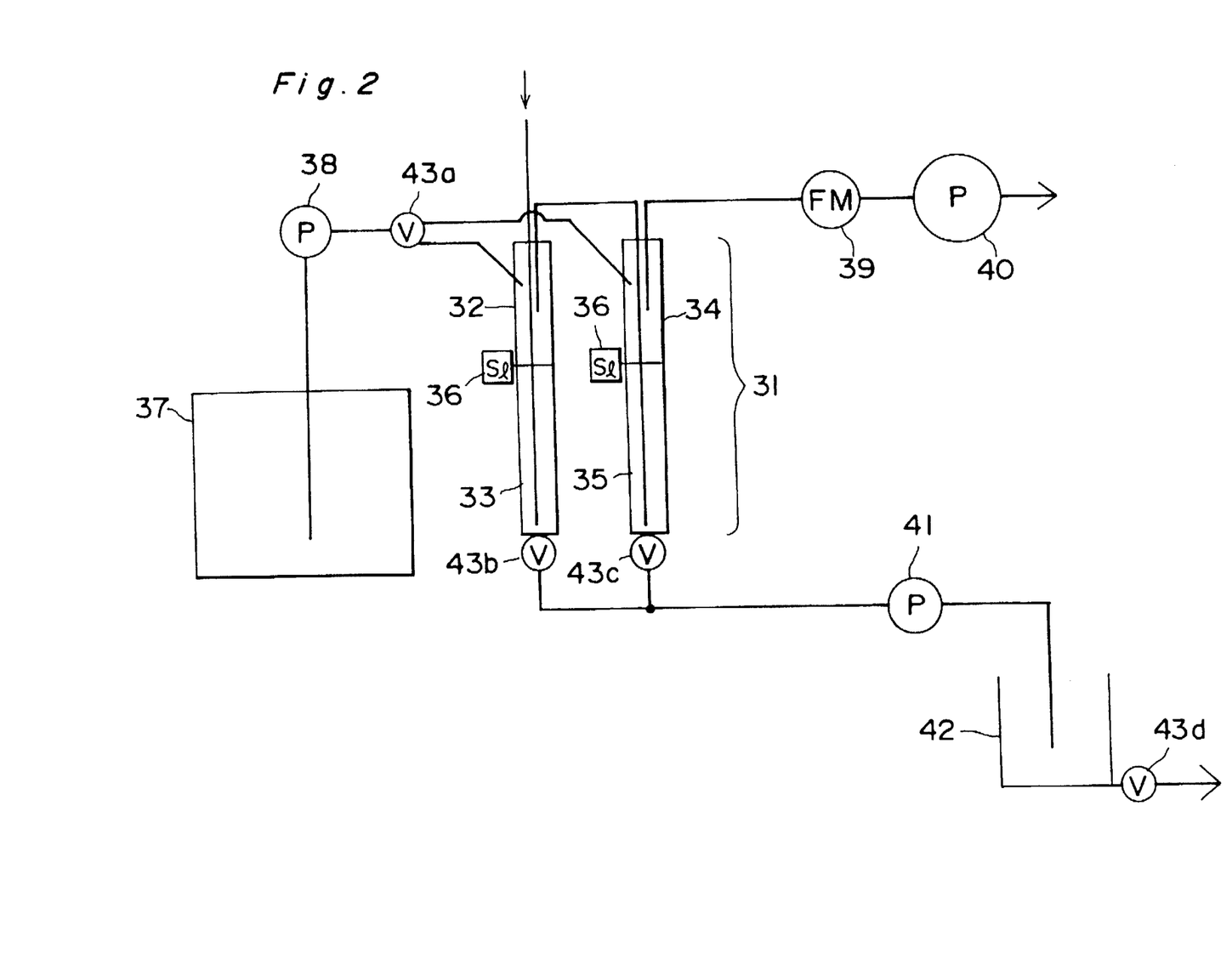
FIG. 2 is a schematic view of an in-atmosphere impurity automatic analysis apparatus of the present invention.

This in-atmosphere impurity state-by-state analysis apparatus has a general construction such that a joint tube 49 of the gas component collecting section 45, which is the same construction as that of the gas component collecting section 21 in the in-atmosphere impurity collecting apparatus shown in FIG. 1, is connected to the atmosphere sample intake of an analysis apparatus, which is the same construction as that of the in-atmosphere impurity automatic analysis apparatus shown in FIG. 2. An upper portion of the gas component collecting use absorption liquid vessel 48 of the gas component collecting section 45 is connected with a liquid transfer on-off valve 61a of the above analysis apparatus via a liquid transfer pipe, while a bottom portion of the gas component collecting use absorption liquid vessel 48 of the gas component collecting section 45 is connected with the downstream side of the particle component collecting use liquid transfer pump 59 of the above analysis apparatus via a bifurcated liquid transfer pipe provided with interposition of liquid transfer on-off valves 61e through 61g.

This in-atmosphere impurity state-by-state analysis apparatus operates as follows to execute automatic state-by-state monitoring of the impurities in the atmosphere in real time.

First, the atmosphere sample suction pump 58 with flow meter 57 is driven to take in an atmosphere sample at a specified flow rate into a gas component permeable membrane tube 47 of the gas component collecting section 45. As the atmosphere sample passes through the gas component collecting section 45, only the gas component of the atmosphere sample is taken out of the gas component permeable membrane tube 47 and then collected into the gas component collecting use absorption liquid 48a. Then the atmosphere sample being rid of only the gas component is introduced into a particle component collecting section 46 via the joint tube 49.

The atmosphere being rid of the gas component is subjected to bubbling in a first stage impinger section 50 of the particle component collecting section 46, so that the particle component is collected into a first stage particle component collecting use absorption liquid 51. Further, each particle component which has not been collected in the first stage impinger section 50 is subjected to bubbling again in a second stage impinger section 52 to be collected into a second stage particle component collecting use absorption liquid 53; reference numeral 54 indicates a surface sensor therein.

It is to be noted that the gas component collecting use absorption liquid 48a and both the particle component collecting use absorption liquids 51 and 53 are supplied from an absorption liquid supply tank 55 via the liquid transfer on-off valve 61a by a specified amount in each time of measurement by the absorption liquid supply use liquid transfer pump 56.

As described above, when the atmosphere sample is drawn in by suction for a specified time to complete the collecting of the components, firstly the gas component collecting use absorption liquid 48a is introduced into an analysis apparatus 62 such as a two-way simultaneous measurement ion chromato-analyzer based on, for example, a condensed column method upon opening the liquid transfer on-off valves 61f and 61g, and is then subjected to measurement after being condensed.

On the other hand, both the particle component collecting use absorption liquids 51 and 53 are temporarily introduced into a particle component measurement standby vessel 60 to wait for the measurement time by the particle component collecting use liquid transfer pump 59 upon opening the liquid transfer on-off valves 61b, 61c and 61e. Then, after the above mentioned measurement of the gas component collecting use absorption liquid 48a is completed, the adsorption liquid in the vessel 60 is introduced into the analysis apparatus 62 to be condensed and measured.

By repeating the above operations, the state-by-state automatic monitoring of the impurities as both gas and particle components in the atmosphere is performed in real time.

Figure 4:
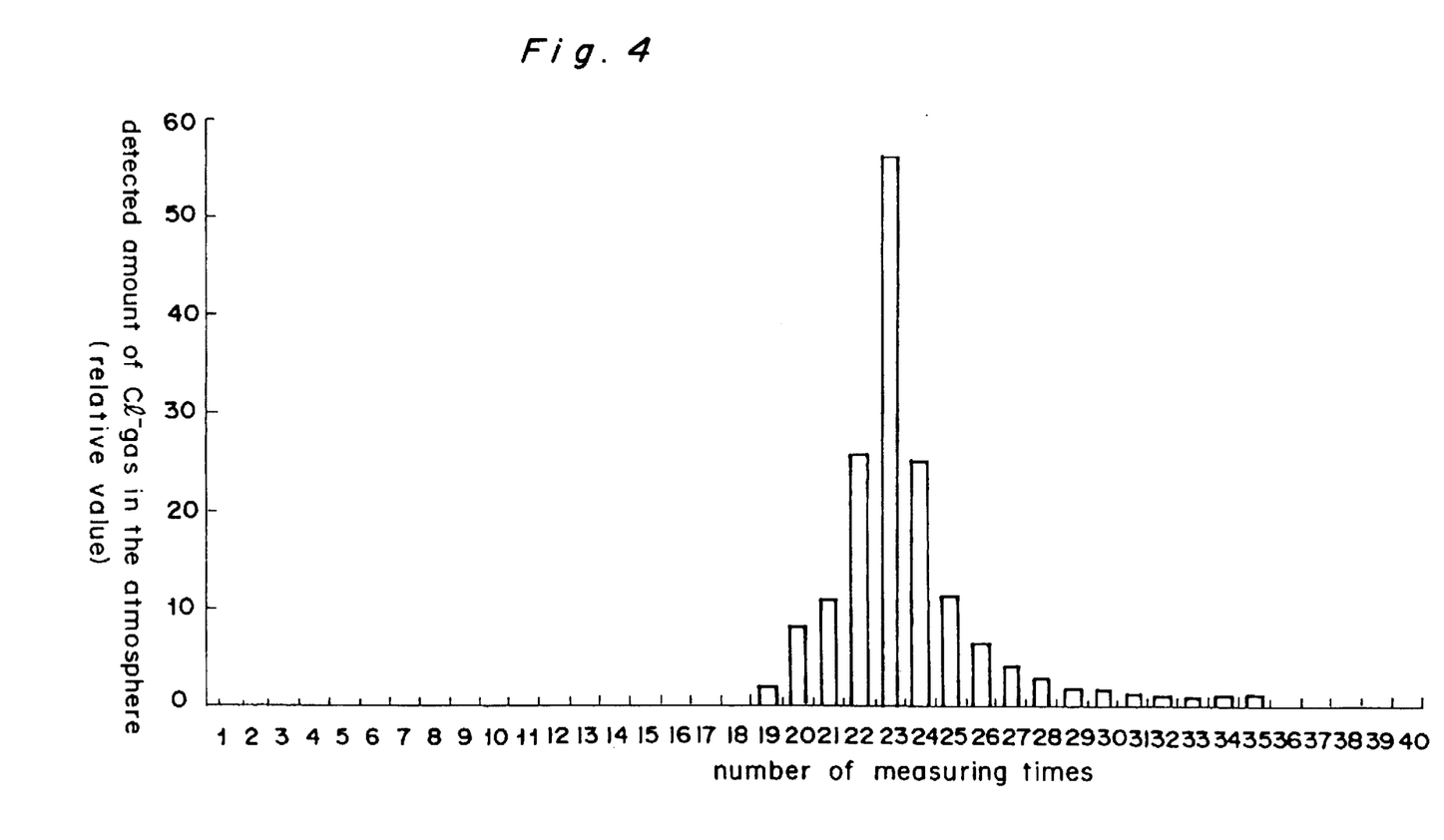
FIG. 4 is a graph showing an example of real time monitoring of a Cl⁻ gas component in the atmosphere by the in-atmosphere impurity state-by-state analysis apparatus shown in FIG. 3.

FIG. 4 shows an example of the real time monitoring of a Cl⁻ gas component in the atmosphere.

In FIG. 4, the amount of the Cl⁻ gas component in the atmosphere increases at and around the 23th time of measurement, and this indicates the occurrence of a certain contamination. Therefore, it can be presumed that the apparatus processed at the 23th time of measurement is the source of contamination.

The above implies that the present in-atmosphere impurity state-by-state analysis apparatus is very effective in ascertaining the contamination source in real time.

Figure 5:
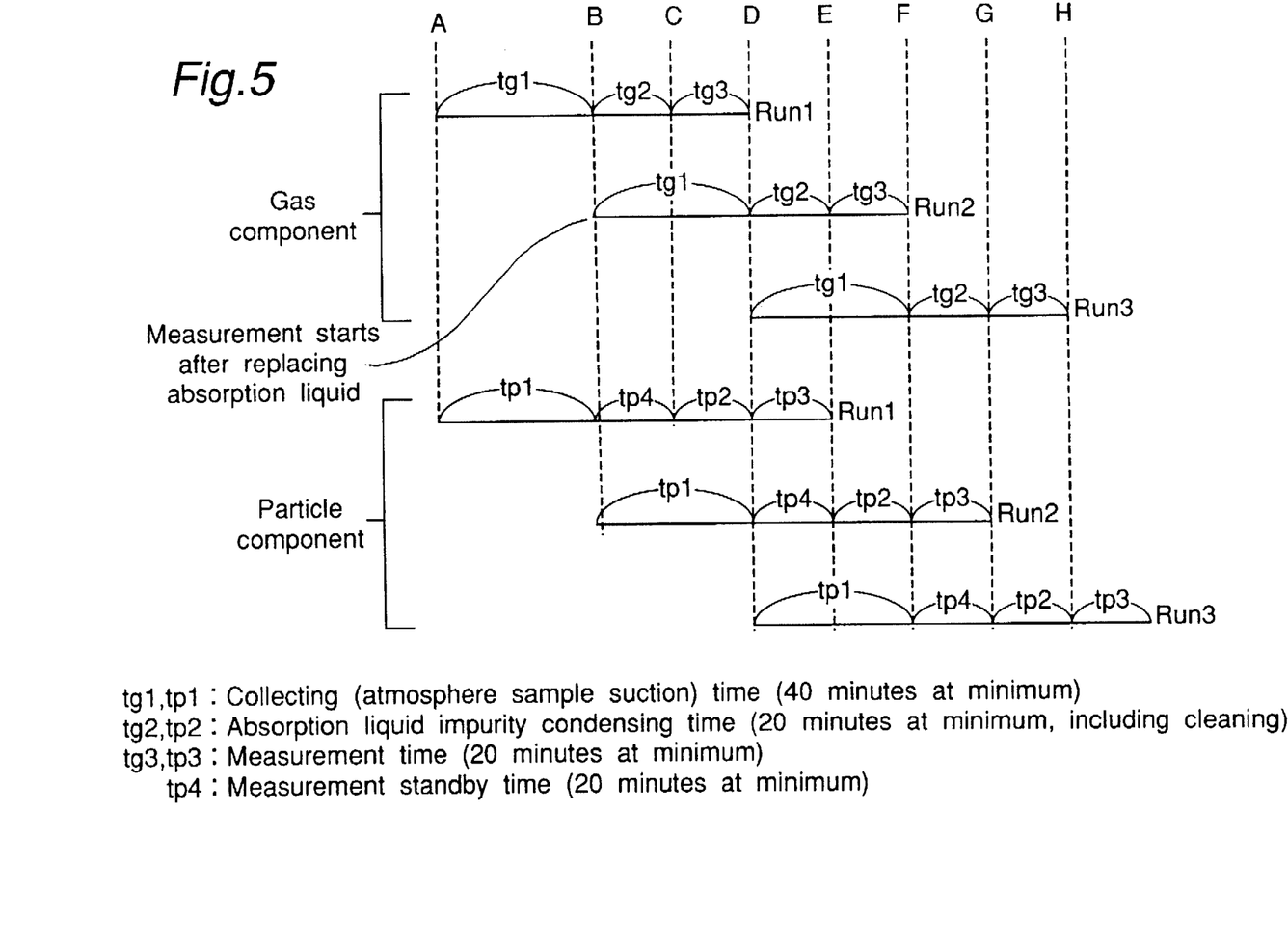
FIG. 5 is a view of a time table of the in-atmosphere impurity state-by-state automatic monitoring executed by the in-atmosphere impurity state-by-state analysis apparatus shown in FIG. 3.

The present in-atmosphere impurity state-by-state analysis apparatus operates according to a time table as shown in FIG. 5 to perform the state-by-state automatic monitoring of the impurities in the atmosphere under the control of a computer or the like.

The time table in FIG. 5 shows the first time (Run 1) through the third time (Run 3) of the collecting, standby, condensation and measurement by the gas component and the particle component, and this time table will be repeated in the fourth and subsequent times.

It is to be noted that the symbols in FIG. 5 indicate the following items.

Time table of gas component:

tg1: Collecting by means of the gas component collecting section 45 tg2: Condensation of the gas component collecting use absorption liquid 48a by the analysis apparatus 62 tg3: Measurement by the analysis apparatus 62

Time table of particle component:

tp1: Collecting by means of the particle component collecting section 46 tp2: Condensation of the particle component collecting use absorption liquids 51 and 53 by the analysis apparatus 62 tp3: Measurement by the analysis apparatus 62 tp4: Standby for measurement

At the time point A in the above time table, the first time collecting (tg1-1) of the gas component and the first time collecting (tp1-1) of the particle component are started simultaneously.

At a time point B, the first time condensation (tg2-1) of the gas component collecting use absorption liquid 48a and the first time transfer (tp4-1) of the particle component collecting use absorption liquids 51 and 53 to the particle component measurement standby vessel 60 are executed simultaneously. At the same time, new absorption liquid is supplied to the emptied gas component collecting use absorption liquid vessel 48 and to the first and second stage impinger sections 50 and 52, and then the second time collecting (tg1-2) of the gas component and the second time collecting (tp1-2) of the particle component are also started.

At a time point C, the first time measurement (tg3-1) of the gas component collecting use absorption liquid 48a and the first time condensation (tp2-1) of the particle component collecting use absorption liquids 51 and 53 are executed simultaneously.

At a time point D, the first time measurement (tp3-1) of the particle component collecting use absorption liquids 51 and 53 is executed. At the same time, the second time condensation (tg2-2) of the gas component collecting use absorption liquid 48a and the second time transfer (tp4-2) of the particle component collecting use absorption liquids 51 and 53 to the particle component measurement standby vessel 60 are also executed. Simultaneously, the third time collecting (tg1-3) of the gas component and the third time collecting (tp1-3) of the particle component are also started.

Thus, the first time collecting and measurement of the impurities in the atmosphere is executed at the time point A through the time point E.

At the time point E, the second time measurement (tg3-2) of the gas component collecting use absorption liquid 48a and the second time condensation (tp2-2) of the particle component collecting use absorption liquids 51 and 53 are executed simultaneously.

At a time point F, the second time measurement (tp3-2) of the particle component collecting use absorption liquids 51 and 53 is executed. At the same time, the third time condensation (tg2-3) of the gas component collecting use absorption liquid 48a and the third time transfer (tp4-3) of the particle component collecting use absorption liquids 51 and 53 to the particle component measurement standby vessel 60 are executed.

Thus, the second time collecting and measurement of the impurities in the atmosphere is executed at the time point B through the time point G.

At the time point G, the third time measurement (tg3-3) of the gas component collecting use absorption liquid 48a and the third time condensation (tp2-3) of the particle component collecting use absorption liquids 51 and are executed simultaneously.

At a time point H, the third time measurement (tp3-3) of the particle component collecting use absorption liquids 51 and 53 is executed.

Thus, the third time collecting and measurement of the impurities in the atmosphere that has been started at the time point D is completed.

That is, according to the above time table, by executing the collecting of the atmosphere for the gas component or the particle component in 40 minutes at minimum and executing the other operations of condensation, measurement and standby in 20 minutes at minimum, the operation sequence from the collecting of the atmosphere for the gas component or the particle component to the condensation and measurement of the components can be executed in parallel while shifting the timing by 40 minutes at minimum.

As a result, the collecting of the atmosphere is executed every 40 minutes, so that the measurement result of the gas component is obtained after the elapse of 40 minutes from the completion of the collecting, and the measurement result of the particle component is obtained after the elapse of 60 minutes from the completion of the collecting.

It is to be noted that, after the gas component collecting use absorption liquid 48a and the particle component collecting use absorption liquids 51 and 53 are transferred to the analysis apparatus 62 or the particle component measurement standby vessel 60 by operating the liquid transfer on-off valves 61f and 61g, operating the liquid transfer on-off valves 61b, 61c and 61e and driving the particle component collecting use liquid transfer pump 59, the gas component collecting use absorption liquid 48a and the particle component collecting use absorption liquids 51 and 53 are supplied by operating the liquid transfer on-off valve 61a and driving the absorption liquid supply use liquid transfer pump 56. Thus, replacement of the absorption liquids inside the gas component collecting use absorption liquid vessel 48 and the first and second stage impinger sections 50 and 52 are executed.

In this case, the time required for the replacement of the absorption liquids is several tens of seconds. Therefore, taking into account the fact that the minimum measurement time is 40 minutes as described above, it can be said that the loss time required for the replacement of the absorption liquids does not exert a great influence on the measurement results.

Furthermore, as described above, the collecting use absorption liquids 48a, 51 and 53 in the gas component collecting use absorption liquid vessel 48, the first stage impinger section 50 and the second stage impinger section 52 are replaced in accordance with the timing of opening and closing the liquid transfer on-off valves 61a through 61g in each time of measurement, so that the gas component collecting use absorption liquid vessel 48 and both the impinger sections 50 and 52 are cleaned. That is, the present in-atmosphere impurity state-by-state analysis apparatus has a cleaning function.

Thus, according to the present in-atmosphere impurity state-by-state analysis apparatus, which has the in-atmosphere impurity collecting apparatus shown in FIG. 1, first the gas component in the atmosphere sample is collected into the gas component collecting use absorption liquid 48a by drawing the atmosphere sample into the gas component collecting section 45 by means of the atmosphere sample suction pump 58, and secondly the particle component is collected into the particle component collecting use absorption liquids 51 and 53 in the particle component collecting section 46.

Then, the particle component collecting use absorption liquids 51 and 53 are made to stand by in the particle component measurement standby vessel 60 by driving the particle component collecting use liquid transfer pump 59, while the gas component collecting use absorption liquid 48a is transferred to the analysis apparatus 62 to be condensed and measured. Then new absorption liquid is supplied to the thus emptied gas component collecting use absorption liquid vessel 48 and the first and second stage impinger sections 50 and 52 by driving the absorption liquid supply use liquid transfer pump 56, and the next atmosphere sample is started to be drawn in by suction.

When the measurement of the gas component collecting use absorption liquid 48a is completed in the meantime, the particle component collecting use absorption liquids 51 and 53 that are standing by in the particle component measurement standby vessel 60 are transferred to the analysis apparatus 62 to be condensed and measured.

Therefore, according to the present in-atmosphere impurity state-by-state analysis apparatus, the collecting, condensation and measurement can be executed in parallel by the gas component and the particle component with a timing shift according to the time table shown in FIG. 5, thereby allowing the state-by-state automatic monitoring of the impurities in the atmosphere to be repetitively performed in real time.

It is generally said that the in-atmosphere impurity collecting method by means of an impinger requires a long collecting time (atmosphere sample suction time) due to its degraded sensitivity. However, each of the first and second stage impinger sections 50 and 52 of the present in-atmosphere impurity state-by-state analysis apparatus has a shape elongated more than that of the prior art impinger for the purpose of assuring a longer time of contact of the atmosphere with the particle component collecting use absorption liquids 51 and 53. Therefore, it is not required to extend the collecting time.

Furthermore, by using the analysis apparatus based on the condensed column method as the analysis apparatus 62, a small amount of impurities can be measured even in a short collecting time.

It is to be noted that the contents of the absorption liquids 48a, 51 and 53 are not limited to those of the present embodiment. Furthermore, different analysis apparatuses 62 may be used for the gas component and the particle component.

For example, when measuring metal impurities such as Fe, Cr, Ni and the like other than the acid component and the ammonium component in the above in-atmosphere impurity state-by-state analysis apparatus, it is proper to use a diluted acid solution for the particle component collecting use absorption liquids 51 and 53 and measure the particle component collecting use absorption liquids 51 and 53 that have been introduced into the particle component measurement standby vessel 60 by introducing them into an ICP-AES (Inductively Coupled Plasma-Atomic Emission Spectrometer), an ICP-MS (Inductively Coupled Plasma-Mass Spectrometer) or an FL-AAS (Flameless Atomic Absorption Spectrometer) and the like.

A clean room in-atmosphere impurity monitoring apparatus employing the in-atmosphere impurity state-by-state analysis apparatus shown in FIG. 3 will be described next.

Figure 6:
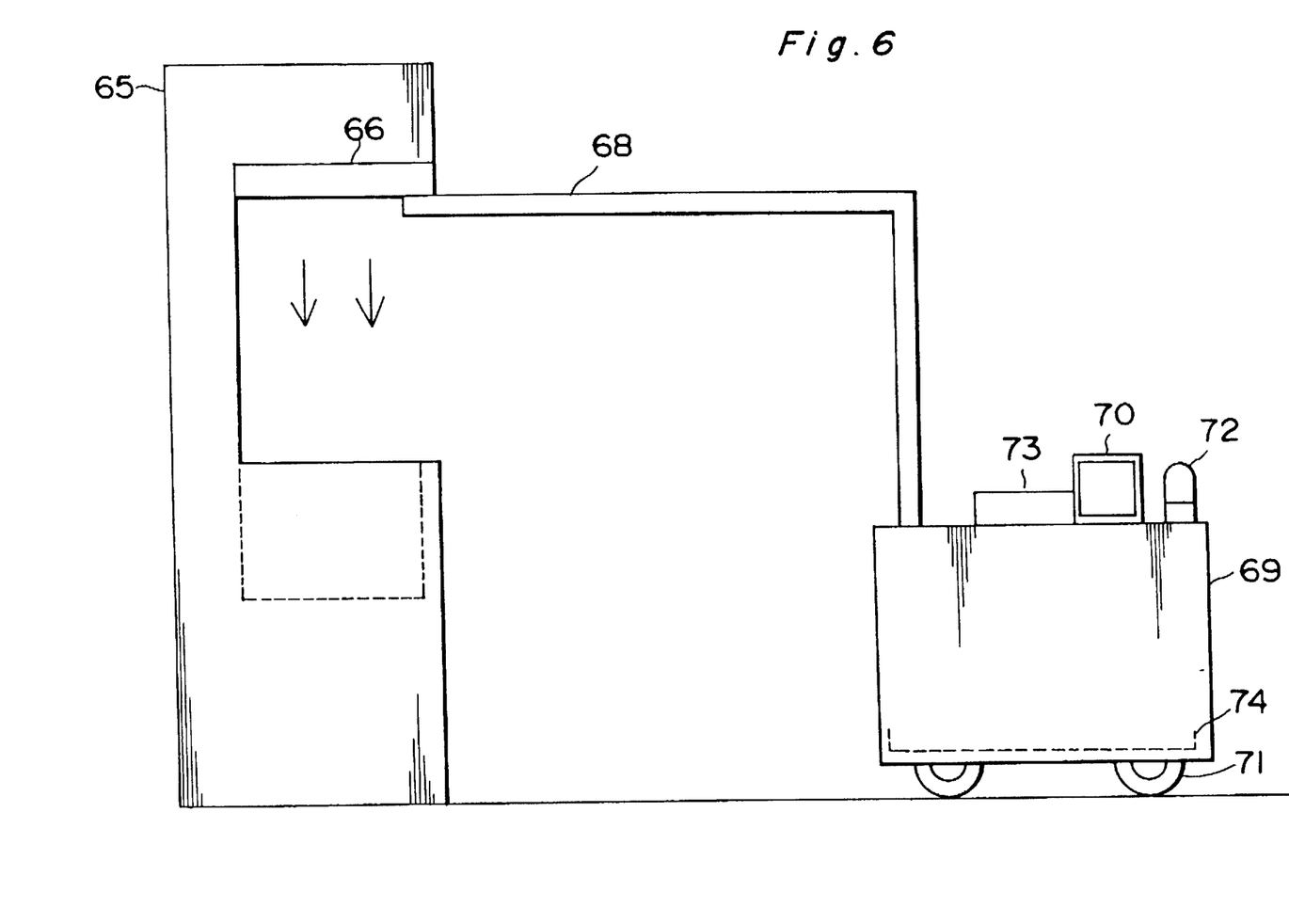
FIG. 6 is an external view of an apparatus for monitoring impurities in the atmosphere in a clean room.

FIG. 6 is a schematic view of the clean room in-atmosphere impurity monitoring apparatus.

This clean room in-atmosphere impurity monitoring apparatus is used for correctly perceiving the time of replacement of an HEPA filter unit 66 mounted to a production processing apparatus 65.

Figure 3:
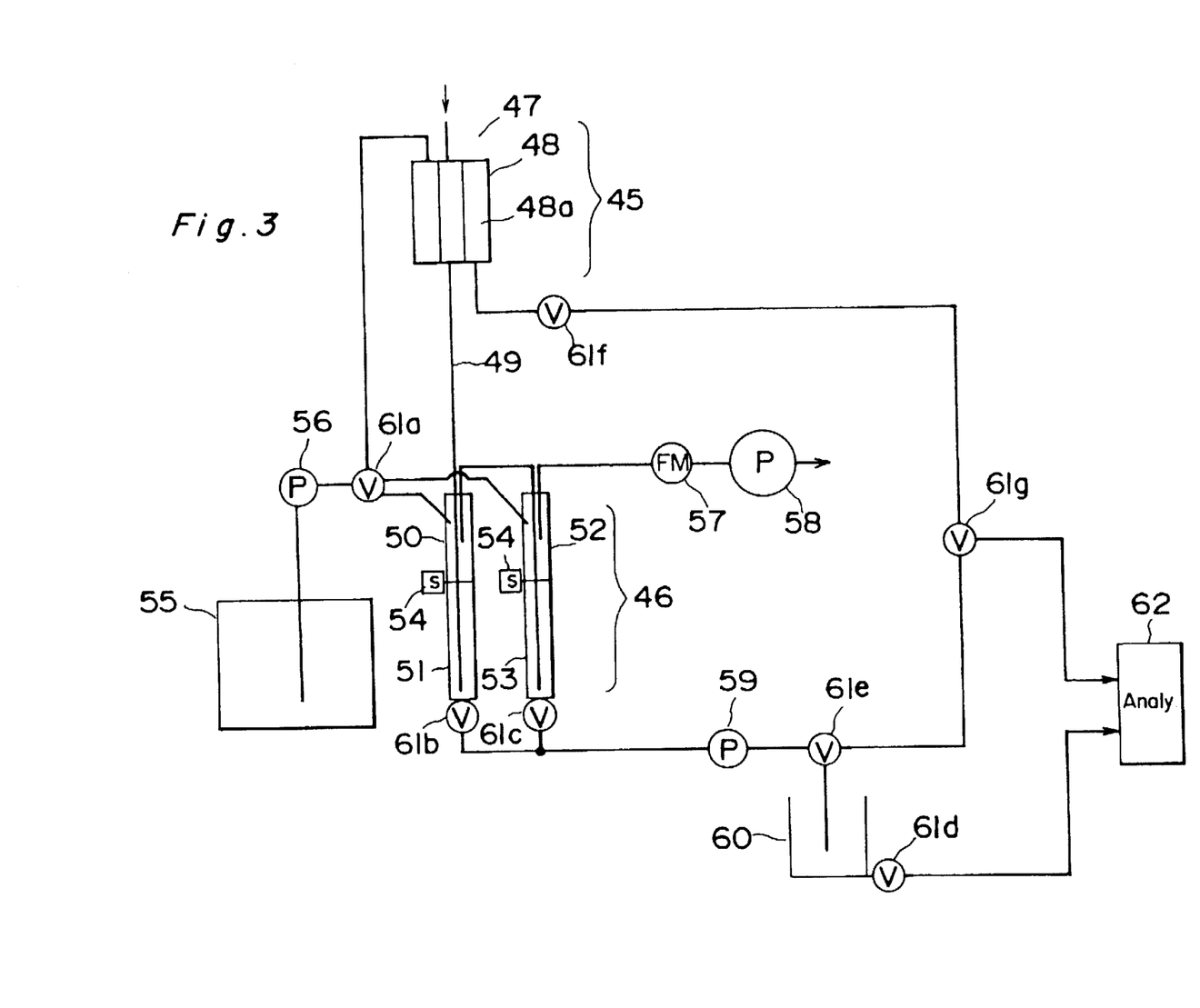
FIG. 3 is a schematic view of an in-atmosphere impurity state-by-state analysis apparatus of the present invention.

In its main body 69 is stored an in-atmosphere impurity state-by-state analysis apparatus (not shown) identical to the in-atmosphere impurity state-by-state analysis apparatus shown in FIG. 3. Then, the operations of the atmosphere sample suction pump, the absorption liquid supply use liquid transfer pump, the particle component collecting use absorption liquid transfer pump, and the liquid transfer on-off valves of this in-atmosphere impurity state-by-state analysis apparatus are executed by a control computer 73 according to the time table shown in FIG. 5, so that the monitoring of the impurities in the atmosphere inside the clean room is executed continuously automatically.

The present clean room in-atmosphere impurity monitoring apparatus is further provided with a display 70 for displaying the analysis results of the impurities and a contamination occurrence warning lamp 72 for issuing warning of the occurrence of atmospheric contamination according to the above analysis results.

The clean room in-atmosphere impurity monitoring apparatus constructed as above operates as follows under the control of the control computer 73.

The atmosphere that has been put through the HEPA filter unit 66 of the production processing apparatus 65 is drawn in by suction into the in-atmosphere impurity state-by-state analysis apparatus inside the main body 69 from an atmosphere sample intake pipe 68. Then, the impurities in the atmosphere are analyzed by state according to the time table shown in FIG. 5, and the analysis results are displayed on the display 70 so as to consistently confirm the states of the impurities in the atmosphere. Further, when the density of any impurity exceeds the reference value thereof registered in the memory of the control computer 73, the contamination occurrence warning lamp 72 is lit to inform the operators in surrounding areas of the time of replacement of the HEPA filter unit 66.

It is to be noted that the floor inside the clean room is normally a grating, and therefore, a significant unevenness is present. Therefore, by increasing the diameter of moving wheels 71, the wheels are allowed to easily roll over the unevenness of the floor.

Furthermore, in case of possible leak of the impurity collecting use absorption liquid or the like due to a certain accident, a function of automatically stopping the collecting and analysis as well as a liquid leak preventing tray 74 which receives the leaked absorption liquid or the like are provided.

In the above clean room in-atmosphere impurity monitoring apparatus, the in-atmosphere impurity state-by-state analysis apparatus identical to the in-atmosphere impurity state-by-state analysis apparatus shown in FIG. 3 is stored in the main body 69. However, if the state-by-state analysis is not specifically required, an in-atmosphere impurity automatic analysis apparatus identical to the in-atmosphere impurity automatic analysis apparatus shown in FIG. 2 may be stored therein.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An in-atmosphere impurity collecting method comprising the steps of:

introducing an atmosphere into a gas component permeable membrane tube so as to collect a gas component in the atmosphere into a first absorption liquid which is put in contact with an outer peripheral surface of the gas component permeable membrane tube; and introducing into an impinger the atmosphere which has been put inwardly through the gas component permeable membrane tube and from which the gas component has been collected and subjecting the atmosphere to bubbling in a second absorption liquid so as to collect a particle component in the atmosphere;

thereby collecting impurities in the atmosphere as the gas component and the particle component separately from each other.

2. An in-atmosphere impurity automatic analysis apparatus comprising:

an impinger which receives therein an absorption liquid for impurities in an atmosphere;

a suction pump which sucks a gas inside the impinger to take the atmosphere into the impinger and subjects the atmosphere to bubbling in the absorption liquid so that it collects the impurities in the atmosphere;

a first liquid transfer pump which transfers the absorption liquid containing the impurities in the atmosphere to an analysis apparatus;

a second liquid transfer pump which supplies the absorption liquid in an absorption liquid supply tank to the impinger from which the absorption liquid has been transferred; and a control means for controlling operations of the suction pump, the first liquid transfer pump and the second liquid transfer pump to make them execute continuously repetitively the collecting of the impurities in the atmosphere, the transfer of the absorption liquid to the analysis apparatus and the supply of the absorption liquid.

3. An in-atmosphere impurity state-by-state analysis apparatus comprising:

a gas component collecting section which comprises a cylindrical gas component absorption liquid vessel whose both ends are closed, a gas component permeable membrane tube which is inserted in the gas component absorption liquid vessel with its both ends fitted close to both end surfaces of the gas component absorption liquid vessel, and a gas component absorption liquid which is filled inside the gas component absorption liquid vessel while being put in contact with an outer peripheral surface of the gas component permeable membrane tube, wherein the gas component absorption liquid vessel has at its one and the other end surfaces an atmosphere -inlet and -outlet respectively which communicate with the inside of the gas component permeable membrane tube;

an impinger which receives therein a particle component absorption liquid and of which the atmosphere intake communicates with the atmosphere-outlet of the gas component collecting section;

a suction pump which sucks the gas inside the impinger to take the atmosphere into the gas component permeable membrane tube, make the gas component absorption liquid collect the gas component in the atmosphere, and thereafter take the atmosphere being rid of the gas component into the impinger to subject the atmosphere to bubbling in the particle component absorption liquid so that it collects a particle component in the atmosphere;

a first liquid transfer means for transferring the particle component absorption liquid containing the particle component to a measurement standby vessel so as to make the liquid stand by;

a second liquid transfer means for transferring the gas component absorption liquid containing the gas component to the analysis apparatus while the particle component absorption liquid is made to stand by;

a third liquid transfer means for supplying the absorption liquid in an absorption liquid supply tank to the gas component absorption liquid vessel and to the impinger when the absorption liquid inside the gas component absorption liquid vessel and the adsorption liquid inside the impinger are transferred;

a fourth liquid transfer means for transferring the particle component absorption liquid that is standing by in the measurement standby vessel to the analysis apparatus when the analysis of the gas component absorption liquid by the analysis apparatus is completed; and a control means for controlling operations of the suction pump and the first through fourth liquid transfer means to make them execute continuously repetitively the collecting of the impurities in the atmosphere by the gas component and the particle component, the standing-by of the particle component absorption liquid, the transfer of each absorption liquid to the analysis apparatus and the supply of the absorption liquid to the gas component absorption liquid vessel and the impinger.

* * * * *